(12) United States Patent
Baltz et al.

(10) Patent No.: US 6,452,069 B1
(45) Date of Patent: Sep. 17, 2002

(54) SF3 PROMOTER AND METHODS OF USE

(75) Inventors: Rachel Yvonne Baltz, Strasbourg (FR); Dennis L. Bidney, Urbandale, IA (US); Gary A. Huffman, Des Moines, IA (US); Guihua Lu, Urbandale, IA (US); Christopher J. Scelonge, Des Moines, IA (US); Andre A. Steinmetz, Strassen (LU)

(73) Assignee: Pioneer Hi-Bred International, Inc., Des Moines, IA (US)

(*) Notice: Subject to any disclaimer, the term of this patent is extended or adjusted under 35 U.S.C. 154(b) by 0 days.

(21) Appl. No.: 09/524,168

(22) Filed: Mar. 13, 2000

Related U.S. Application Data
(60) Provisional application No. 60/124,634, filed on Mar. 16, 1999, and provisional application No. 60/128,317, filed on Apr. 8, 1999.

(51) Int. Cl.$^7$ ............................ C12N 15/11; C12N 5/10; C12N 15/82; C12N 15/29; A01H 5/00
(52) U.S. Cl. ................... 800/287; 800/278; 800/298; 800/322; 800/320.1; 435/419; 435/468; 435/320.1; 435/412; 435/416; 536/24.1; 536/23.6
(58) Field of Search .............................. 536/24.1, 23.6; 800/287, 279, 298, 303, 322, 302; 435/320.1, 419, 468, 412, 416

(56) References Cited

U.S. PATENT DOCUMENTS

| | | |
|---|---|---|
| 5,086,169 A | 2/1992 | Mascarenhas |
| 5,545,546 A | 8/1996 | Allen et al. |
| 5,728,926 A | 3/1998 | Fabijanski et al. |
| 5,795,753 A | 8/1998 | Cigan et al. |
| 6,037,523 A * | 3/2000 | Albertsen et al. ........... 800/287 |

OTHER PUBLICATIONS

Baltz, R. et al., Accession No. AF187104, 1992.*
Doelling, J. H. and Pikaard, C. S. "The minimal ribosomal RNA gene promoter of *Arabidopsis thaliana* includes a critical element at the transcription initiation site." 1995, The Plant Journal, vol. 8, pp. 683–692.*

Maiti, I. B. et al., "Promoter/leader deletion analysis and plant expression vectors with the figwort mosaic virus (FMV) full length transcript (FLt) promoter containing single or double enhancer domain." 1997, Transgenic Res., vol. 6, pp. 143–156.*

Donald, R. G. K. and Cashmore, A. R. "Mutation of either G box or I box sequences profoundly affects expression from the Arabidopsis rbcS–1A promoter." 1990, The EMBO Journal, vol. 9, pp. 1717–1726.*

Eyal, Y. et al., "Pollen Specificity Elements Reside in 30 bp of the Proximal Promoters of Two Pollen–Expressed Genes." 1995, The Plant Cell, vol. 7, pp. 373–384.*

Baltz, R., et al., Characterization of a Pollen–Specific cDNA From Sunflower Encoding a Zinc Finger Protein, The Plant Journal, (1992), vol. 2(5), pp. 713–721.

Baltz, R. et al., The Pollen–Specific LIM Protein PLIM–1 From Sunflower Binds Nucleic Acids in Vitro, Sex Plant Reprod (1996), vol. 9, pp. 264–268.

Baltz, R., et al., A LIM Motif is Present in a Pollen–Specific Protein, (1992) The Plant Cell, vol. 4(12), pp. 1465–1466.

Steinmetz et al. (1996) "Anther–and Pollen–Specific Gene Expression in Sunflower," *Pollen Biotechnology*, pp. 53–66.

\* cited by examiner

*Primary Examiner*—David T. Fox
*Assistant Examiner*—Anne Kubelik
(74) *Attorney, Agent, or Firm*—Alston & Bird LLP

(57) ABSTRACT

The present invention provides compositions and methods for regulating expression of heterologous nucleotide sequences in a plant. Compositions are novel nucleotide sequences for pollen-preferred promoters isolated from a gene unit for SF3. A method for expressing a heterologous nucleotide sequence in a plant using the promoter sequences disclosed herein is provided. The method comprises transforming a plant cell to comprise a heterologous nucleotide sequence operably linked to one of the pollen-preferred promoters of the present invention and regenerating a stably transformed plant from the transformed plant cell.

12 Claims, 4 Drawing Sheets

Plasmid A (6.03kb)

Plasmid B (8.509 kb)

Plasmid C (22.409 kb)

SF3 PROMOTER AND METHODS OF USE

CROSS-REFERENCE TO RELATED APPLICATIONS

This application claims the benefit of U.S. Provisional Applications No. 60/124,634, filed Mar. 16, 1999, and No. 60/128,317, filed Apr. 8, 1999.

FIELD OF THE INVENTION

The present invention relates to the field of plant molecular biology, more particularly to regulation of gene expression in plants.

BACKGROUND OF THE INVENTION

Expression of heterologous DNA sequences in a plant host is dependent upon the presence of an operably linked promoter that is functional within the plant host. Choice of the promoter sequence will determine when and where within the organism the heterologous DNA sequence is expressed. Where continuous expression is desired in cells throughout a plant, promoters driving plant-wide constitutive expression are utilized. In contrast, where gene expression in response to a stimulus is desired, inducible promoters are the regulatory element of choice. Where expression in specific tissues or organs are desired, tissue-preferred promoters may be used. That is, they may drive expression in specific tissues or organs. Expression mediated by such tissue-preferred promoters may be constitutive or inducible. In either case, additional regulatory sequences upstream and/or downstream from the core promoter sequence may be included in expression constructs of transformation vectors to bring about varying levels of expression of heterologous nucleotide sequences in a transgenic plant.

Frequently it is desirable to have constitutive or inducible expression of a DNA sequence in particular tissues or organs of a plant. For example, increased resistance to pathogens of a plant might be accomplished by genetic manipulation of the plant's genome to comprise a tissue-preferred promoter operably linked to a heterologous gene such that proteins which enhance resistance to pathogens are produced in a desired tissue of the plant.

Alternatively, it might be desirable to inhibit expression of a native DNA sequence within a plant's tissues to achieve a desired phenotype. In this case, such inhibition might be accomplished with transformation of the plant to comprise a tissue-preferred promoter operably linked to an antisense nucleotide sequence, such that expression of the antisense sequence produces an RNA transcript that interferes with translation of the mRNA of the native DNA sequence.

The SF3 gene encodes a pollen-specific protein. It has four zinc finger domains organized into two LIM domains. A LIM domain is a double zinc finger in which the last ligand of the first zinc finger is separated from the first ligand of the second zinc finger by two amino acids. The LIM motif could be directly involved in nucleic acid binding. The SF3 protein may be involved in controlling pollen-specific transcription, translation and/or mRNA transport (Baltz et al. (1992) *Plant cell* 4: 1465–1466; Baltz et al. (1996) *Sex. Plant Reprod.* 9: 264–268). A cDNA encoding the SF3 protein has been described in Baltz et al. (1 992) *Plant J.* 2: 713–721.

Manipulation of expression of genes in reproductive tissues of plants can be used to manipulate plant fertility, control pollination and improve hybrid seed production. For example, see U.S. Pat. Nos. 5,795,753; 5,086,169; 5,545,546; 5,728,926.

Thus, isolation and characterization of pollen-preferred promoters that can serve as regulatory regions for expression of heterologous nucleotide sequences of interest in a pollen-preferred manner are useful for genetic manipulation of plants, particularly, for the manipulation of male fertility in plants.

SUMMARY OF THE INVENTION

Compositions and methods for regulating expression of heterologous nucleotide sequences in a plant are provided. The compositions are novel nucleotide sequences for pollen-preferred plant promoters, more particularly the region regulating transcriptional initiation isolated from the plant gene SF3. A method for expressing a heterologous nucleotide sequence in a plant using the transcriptional initiation regulation sequence disclosed herein is provided. The method comprises transforming a plant cell with a transformation vector that comprises a heterologous nucleotide sequence operably linked to the plant promoters of the present invention and regenerating a stably transformed plant from the transformed plant cell. In this manner, the promoter sequences are useful for controlling the expression of endogenous as well as exogenous products in a pollen-preferred manner.

Downstream from and under the transcriptional initiation regulation of the pollen-specific region will be a sequence of interest which will provide for modification of the phenotype of the pollen. Such modification includes modulating the production of an endogenous product, as to amount, relative distribution, or the like or production of an exogenous expression product to provide for a novel function or product in the pollen.

DETAILED DESCRIPTION OF THE INVENTION

Figure 1:
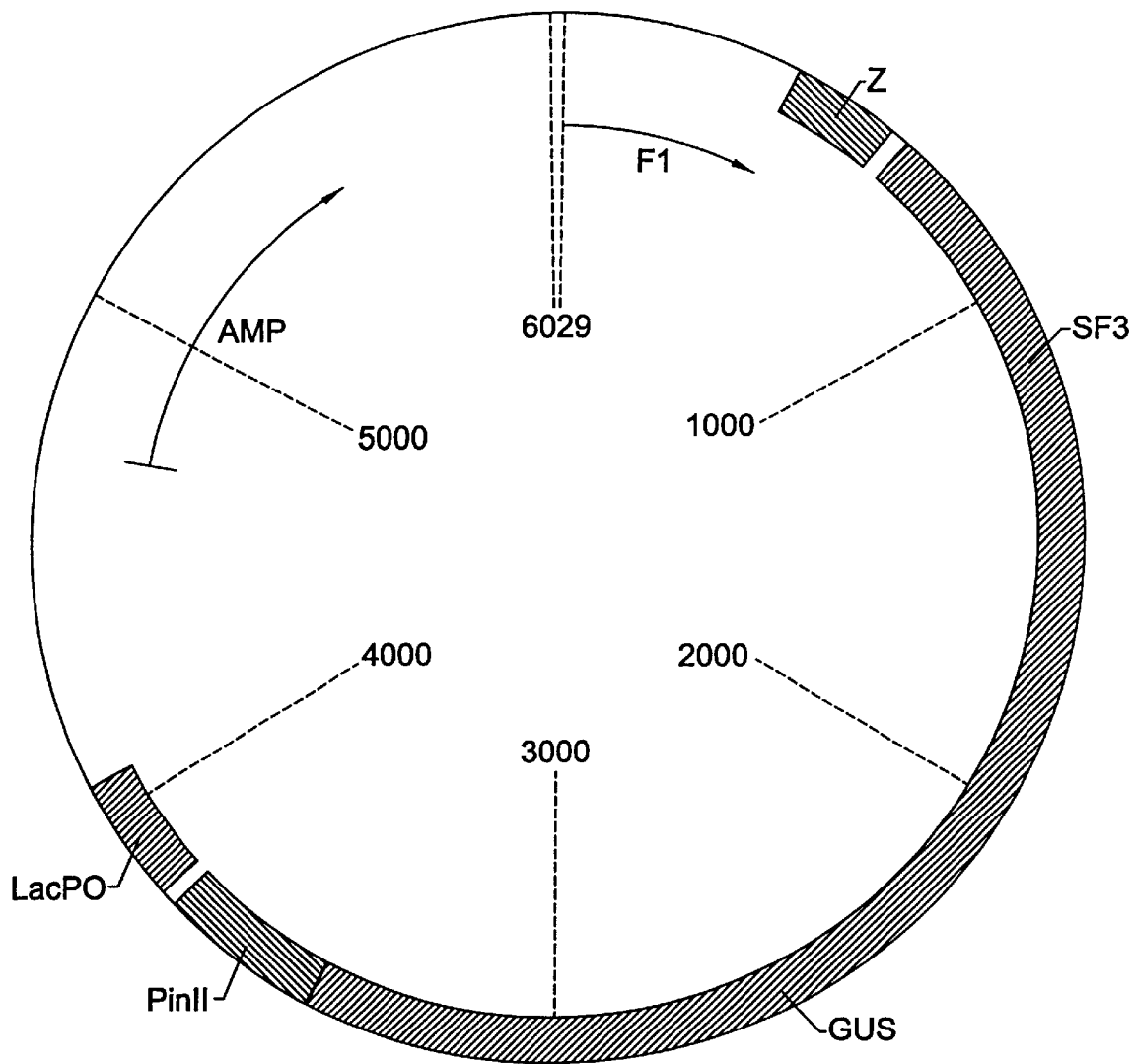
FIG. 1 schematically depicts a construct comprising the plant transcription unit PSF3:GUS:PINII-3'.

In accordance with the invention nucleotide constructs are provided that allow initiation of transcription in pollen. Constructs of the invention comprise regulated transcriptional initiation regions associated with pollen formation and, pollen tissues. Thus, the compositions of the present invention comprise novel nucleotide sequences for plant promoters, more particularly pollen-preferred promoters, and even more particularly pollen-preferred promoters for SF3 genes.

In particular, the present invention provides for isolated nucleic acid molecules comprising the nucleotide sequences shown in SEQ ID NOs:1 and 2, or the nucleotide sequences encoding the DNA sequences in a bacterial host as Patent Deposit No. 203856; and fragments and variants thereof.

Plasmids containing the nucleotide sequences of the invention were deposited with the Patent Depository of the American Type Culture Collection (ATCC), Manassas, Va., on Mar. 17, 1999 and assigned Patent Deposit No. 203856. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

The invention encompasses isolated or substantially purified nucleic acid compositions. An "isolated" or "purified" nucleic acid molecule, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

The promoters for SF3 genes may be generally isolated from the 5' untranslated region flanking their respective transcription initiation sites. Methods for isolation of promoter regions are well known in the art. By "isolated" is intended that the promoter sequences have been determined and can be extracted by molecular techniques or synthesized by chemical means. In either instance, the promoter is removed from at least one of its flanking sequences in its native state.

It is recognized that regions in addition to the promoter region may be used to initiate transcription. Such regions include the untranslated region (UTR) and even portions of the coding sequence particularly 5' portions of the coding region. Generally, from about 3 nucleotides (1 codon) up to about 150 nucleotides (50 codons) of the 5' coding region can be used. See, for example, McElroy et al. (1991) *Mol. Gen. Genet.* 231:150–160 where expression vectors were constructed based on the rice actin1 5' region.

The 5' untranslated leader region for the SF3 gene from sunflower is shown in SEQ ID NO:2 as residues 825 to 928.

Fragments and variants of the disclosed nucleotide sequences are also encompassed by the present invention. By "fragment" is intended a portion of the nucleotide sequence. Fragments of a nucleotide sequence may retain biological activity and drive expression, particularly pollen-preferred expression. Alternatively, fragments of a nucleotide sequence that are useful as hybridization probes generally do not retain biological activity. Thus, fragments of a nucleotide sequence may range from at least about 24 nucleotides, about 50 nucleotides, about 100 nucleotides, and up to the full-length nucleotide of the invention.

Thus, a fragment of a nucleotide sequence for promoters for SF3 genes may encode a biologically active portion of a SF3 promoter, or it may be a fragment that can be used as a hybridization probe or PCR primer using methods disclosed below. A biologically active portion of a SF3 promoter can be prepared by isolating a portion of the SF3 promoter nucleotide sequences of the invention, and assessing the activity of the portion of the SF3 promoter. Nucleic acid molecules that are fragments of a SF3 promoter nucleotide sequence comprise at least 24, 50, 75, 100, 150, 200, 250, 300, 350, 400, 450, 500, 550, 600, 650, 700, 800) nucleotides, or up to the number of nucleotides present in a full-length SF3 promoter nucleotide sequence disclosed herein (for example, 824 nucleotides for SEQ ID NO: 1.

By "variants" is intended substantially similar sequences. For nucleotide sequences, naturally occurring variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis. Generally, variants of a particular nucleotide sequence of the invention will have at least 70%, generally at least 75%, 80%, 85%, preferably about 90% to 95% or more, and more preferably about 98% or more sequence identity to that particular nucleotide sequence as determined by sequence alignment programs described elsewhere herein using default parameters. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein.

Variant nucleotide sequences also encompass sequences derived from a mutagenic and recombinogenic procedure such as DNA shuffling. With such a procedure, one or more different promoter sequences, including the SF3 promoter sequences of the invention, can be manipulated to create a new promoter sequence possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Preferred, non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad. Sci.* 85:2444–2448; the algorithm of Karlin and Altschul (1990) *Proc. Natl. Acad. Sci. USA* 872264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, California); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237–244 (1988); Higgins et al. (1989) CABIOS 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. A PAM 120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.nlm.nih.gov. Alignment may also be performed manually by inspection.

For purposes of the present invention, comparison of nucleotide or protein sequences for determination of percent sequence identity to the SF3 promoter sequences disclosed herein is preferably made using the GCG program GAP (Version 10.00 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of I and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The nucleotide sequences of the invention can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire SF3 sequences set forth herein or to fragments thereof are encompassed by the present invention. Comparable promoter regions from other oraganisms, including other plants, may be obtained by utilization of the coding or promoter sequences set forth herein. Using the SF3 coding sequences, other pollen-preferred promoters can be isolated by obtaining regions 5' to the regions of homology.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the SF3 sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire SF3 promoter sequence disclosed herein, or one or more portions thereof, may be used as a probe capable of specifically hybridizing to corresponding promoter sequences. To achieve specific hybridization under a variety of conditions, such probes include sequences that are unique among SF3 promoter sequences and are preferably at least about 10 nucleotides in length, and most preferably at least about 20 nucleotides in length. Such probes may be used to amplify corresponding promoter sequences from a chosen plant by PCR. This technique may be used to isolate additional promoter sequences from a desired plant or as a diagnostic assay to determine the presence of the promoter sequences in a plant.

Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2× SSC (20× SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1× SSC at 55 to 60° C. Exemplary high stringency conditions include hybridization in 50% formamide, 1 M NaCl, 1% SDS at 37° C., and a wash in 0.1× SSC at 60 to 65° C. Duration of hybridization is generally less than about 24 hours, usually about 4 to about 12 hours.

Specificity is typically the function of post-hybridization washes, the critical factors being the ionic strength and temperature of the final wash solution. For DNA—DNA hybrids, the $T_m$ can be approximated from the equation of Meinkoth and Wahl (1984) *Anal. Biochem.* 138:267–284: $T_m$=81.5° C.+16.6 (log M)+0.41 (% GC)−0.61 (% form)−

500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al, eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.). Thus, isolated sequences that have promoter activity and which hybridize under stringent conditions to the SF3 sequences disclosed herein, or to fragments thereof, are encompassed by the present invention. Such sequences will be at least 40% to 50% homologous, about 60% to 70% homologous, and even about 75%, 80%, 85%, 90%, 95% to 98% homologous or more with the disclosed sequences. That is, the sequence identity of sequences may range, sharing at least 40% to 50%, about 60% to 70%, and even about 75%, 80%, 85%, 90%, 95% to 98% or more sequence identity.

The promoter regions of the invention may be isolated from any plant, including, but not limited to corn (*Zea mays*), canola (*Brassica napus, Brassica rapa* ssp.), alfalfa (*Medicago sativa*), rice (*Oryza saliva*), rye (*Secale cereale*), sorghum (*Sorghum bicolor, Sorghum vulgare*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oats, barley, vegetables, ornamentals, and conifers. Preferably, plants include corn, soybean, sunflower, safflower, Brassica, wheat, barley, rye, alfalfa, and sorghum.

The coding sequence expressed by the promoters of the invention may be used for varying the phenotype of the pollen. Various changes in phenotype of interest include but are not limited to arrested pollen development resulting in male sterility or reversible male sterility; resistance to or toxicity of the pollen to insect pests, resistance of the pollen to insecticides and the like. See for example U.S. Pat. Nos. 5,795,753; 5,086,169; 5,545,546; and 5,728,926.

These results can be achieved by providing expression of heterologous or increased expression of endogenous products in pollen. Alternatively, the results can be achieved by providing for a reduction of expression of one or more endogenous products, particularly enzymes and cofactors in the pollen. These changes result in a change in phenotype of the transformed pollen. For example, the promoter sequences of the invention can be used to express suicide genes in pollen and arrest pollen development. Alternatively, the promoter sequences of the invention can be used to produce antisense mRNA complementary to the coding sequence of an essential protein, inhibit production of the protein and cause arrest of pollen development.

General categories of genes of interest for the purposes of the present invention include for example, those genes involved in information, such as Zinc fingers, those involved in communication, such as kinases, and those involved in housekeeping, such as heat shock proteins. It is recognized that the genes of interest depend on the exact specificity of the SF3 promoter.

More specific categories of transgenes, for example, include genes involved in important traits for agronomics, such as fertility, including genes involved in male gamete maturation, pollen tube formation and fertilization; genes involved in resistance to disease, pesticides and insect pests. It is recognized that any gene of interest can be operably linked to the promoter of the invention and expressed in the pollen.

Agronomically important traits such as male sterility and resistance to insect pests can be genetically altered in addition to using traditional breeding methods.

Sterility genes can be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to gametophytic development.

Insect resistance genes may encode resistance to insect pests such as sunflower head moth, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) *Gene* 48:109); lectins (Van Damme et al. (1994) *Plant Mol. Biol.* 24:825); and the like.

Genes encoding disease resistance traits include detoxification genes, such as against fumonosin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

Exogenous products include plant enzymes and products as well as those from other sources including prokaryotes and other eukaryotes. Such products include enzymes, cofactors, hormones, and the like.

As noted, the heterologous nucleotide sequence operably linked to one of the promoters disclosed herein may be an antisense sequence for a targeted gene. Thus, with these promoters, antisense constructions complementary to at least a portion of the messenger RNA (mRNA) for a targeted sequence sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used. Thus, the promoter sequences disclosed herein may be operably linked to antisense DNA sequences to reduce or inhibit expression of a native protein in the plant pollen.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

By "promoter" or "transcriptional initiation region" is intended a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate. It is recognized that having identified the nucleotide sequences for the promoter regions disclosed herein, it is within the state of the art to isolate and identify further regulatory elements in the 5' untranslated region, typically downstream from the particular promoter regions identified herein. Thus, the promoter regions disclosed herein are generally further defined by comprising upstream regulatory elements such as those responsible for tissue and temporal expression of the coding sequence, enhancers and the like. Such elements are typically linked via a 5' untranslated region, which may further modulate gene expression, to a coding region of interest. In the same manner, the promoter elements which enable expression in the desired tissue such as the pollen can be identified, isolated, and used with other core promoters to confirm pollen-preferred expression. For genes in which the 5' untranslated region does not affect cell specificity, alternative sources of 5' untranslated leaders may be used in conjunction with these promoter elements.

The regulatory sequences of the present invention, when operably linked to a heterologous nucleotide sequence of interest and inserted into a transformation vector, enable pollen-preferred expression of the heterologous nucleotide sequence in the pollens of a plant stably transformed with this vector. By "pollen-preferred" is intended that expression of the heterologous sequence is most abundant in the pollen, while some expression may occur in other tissue types.

By "heterologous nucleotide sequence" is intended a sequence that is not naturally occurring with the promoter sequence. While this nucleotide sequence is heterologous to the promoter sequence, it may be homologous, or native, or heterologous, or foreign, to the plant host.

It is recognized that the promoters may be used with their native coding sequences to increase or decrease expression resulting in a change in phenotype in the transformed pollen.

The isolated promoter sequences of the present invention can be modified to provide for a range of expression levels of the heterologous nucleotide sequence. Thus, less than the entire promoter regions may be utilized and the ability to drive pollen-preferred expression retained. However, it is recognized that expression levels of mRNA may be altered and usually decreased with deletions of portions of the promoter sequences. Generally, at least about 20 nucleotides of an isolated promoter sequence will be used to drive expression of a nucleotide sequence.

It is recognized that to increase transcription levels or to alter tissue specificity, enhancers and/or tissue-preferredity elements may be utilized in combination with the promoter regions of the invention. For example, quantitative or tissue specificity upstream elements from other pollen-specific promoters may be combined with the promoter regions of the invention to augment pollen-specific transcription. Such elements have been characterized, for example, for the LAT52, LAT56, and LAT59 promoters from tomato (Twell et al. (1991) *Genes and Development* 5:496–507) and the Zm13 gene of maize (Hamilton et al. (1998) *Plant Mol. Biol.* 38:663–669). The cited promoters have been demonstrated to function transgenically in a non-native dicot species, i.e., tobacco (Guerrero et al. (1990) *Mol. Gen. Genet.* 224:161–168).

Other enhancers are known in the art that would alter the tissue specificity by driving expression in other plant tissues in addition to pollen, such as in the leaves, shoots, vascular tissue, etc. These include, for example, upstream elements from the promoter of the cauliflower mosaic virus 35S transcript, referred to as the 35S promoter, which would give plant-wide vascular-preferred expression in addition to SF3 promoter-mediated expression in pollen. The 35S promoter gives little, if any, expression in pollen. Another example includes upstream elements from promoters of genes encoding the RUBISCO small subunit protein (rbcS) from various species, which would give light-inducible expression in leaf, in addition to SF3-mediated pollen expression. Such patterns of expression could be useful, for example, for obtaining resistance to insects such as head moth or diseases such as sclerotinia.

Modifications of the isolated promoter sequences of the present invention can provide for a range of expression of the heterologous nucleotide sequence. Thus, they may be modified to be weak promoters or strong promoters. Generally, by "weak promoter" is intended a promoter that drives expression of a coding sequence at a low level. By "low level" is intended at levels of about 1/10,000 transcripts to about 1/100,000 transcripts to about 1/500,000 transcripts. conversely, a strong promoter drives expression of a coding sequence at a high level, or at about 1/10 transcripts to about 1/100 transcripts to about 1/1000 transcripts.

The nucleotide sequences for the pollen-preferred promoter disclosed in the present invention, as well as variants and fragments thereof, are useful in the genetic manipulation of any plant when operably linked with a heterologous nucleotide sequence whose expression is to be controlled to achieve a desired phenotypic response. By "operably linked" is intended the transcription of the heterologous nucleotide sequence is under the influence of the promoter sequence. In this manner, the nucleotide sequences for the promoters of the invention may be provided in expression cassettes along with heterologous nucleotide sequences for expression in the plant of interest, more particularly in the pollen of the plant.

Such expression cassettes will comprise a transcriptional initiation region comprising one of the promoter nucleotide sequences of the present invention, or variants or fragments thereof, operably linked to the heterologous nucleotide sequence whose expression is to be controlled by the pollen-preferred promoters disclosed herein. Such an expression cassette is provided with at least one restriction site for insertion of the nucleotide sequence to be under the transcriptional regulation of the regulatory regions. The expression cassette may additionally contain selectable marker genes.

The expression cassette will include in the 5'-to-3' direction of transcription, a transcriptional and translational initiation region, a heterologous nucleotide sequence of interest, and a transcriptional and translational termination region functional in plants. The termination region may be native with the transcriptional initiation region comprising one of the promoter nucleotide sequences of the present invention, may be native with the DNA sequence of interest, or may be derived from another source. Convenient termination regions are available from the Ti-plasmid of *A. tumefaciens*, such as the octopine synthase and nopaline synthase termination regions. See also, Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al (1990) *Plant Cell* 2:1261–1272; Munroe et al. (1990) *Gene* 91:151–158; Ballas et al. 1989) *Nucleic Acids Res.* 17:7891–7903; Joshi et al. (1987) *Nucleic Acid Res.* 15:9627–9639.

The expression cassette comprising the promoter sequence of the present invention operably linked to a heterologous nucleotide sequence may also contain at least one additional nucleotide sequence for a gene to be cotransformed into the organism. Alternatively, the additional sequence(s) can be provided on another expression cassette.

Where appropriate, the heterologous nucleotide sequence whose expression is to be under the control of the promoter sequence of the present invention and any additional nucleotide sequence(s) may be optimized for increased expression in the transformed plant. That is, these nucleotide sequences can be synthesized using plant preferred codons for improved expression. Methods are available in the art for synthesizing plant-preferred nucleotide sequences. See, for example, U.S. Pat. Nos. 5,380,831 and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the heterologous nucleotide sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Nat. Acad. Sci. USA* 86:6126–6130); potyvirus leaders, for example, TEV leader (Tobacco Etch Virus) (Allison et al. (1986)); MDMV leader (Maize Dwarf Mosaic Virus) (*Virology* 154:9–20); human immunoglobulin heavy-chain binding protein (BiP) (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) *Molecular Biology of RNA*, pages 237–256); and maize chlorotic mottle virus leader (MCMV) (Lommel et al. (1991) *Virology* 81:382–385). See also Della-Cioppa et al. (1987) *Plant Physiology* 84:965–968. Other methods known to enhance translation and/or mRNA stability can also be utilized, for example, introns, and the like.

In those instances where it is desirable to have the expressed product of the heterologous nucleotide sequence directed to a particular organelle, particularly the plastid, amyloplast or vacuole, or to the endoplasmic reticulum, or secreted at the cell's surface or extracellularly, the expression cassette may further comprise a coding sequence for a transit peptide. Such transit peptides are well known in the art and include, but are not limited to, the transit peptide for the acyl carrier protein, the small subunit of RUBISCO, plant EPSP synthase, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose; in vitro mutagenesis; primer repair; restriction; annealing; substitutions, for example, transitions and transversions; or any combination thereof may be involved.

Reporter genes or selectable marker genes may be included in the expression cassettes. Examples of suitable reporter genes known in the art can be found in, for example, Jefferson et al. (1991) in *Plant Molecular Biology Manual*, ed. Gelvin et al. (Kluwer Academic Publishers), pp. 1–33; DeWet et al. (1987) *Mol. Cell. Biol.* 7:725–737; Goffet al. (1990) *EMBO J.* 9:2517–2522; Kain et al. (1995) *BioTechniques* 19:650–655; and Chiu et al. (1996) *Current Biology* 6:325–330.

Selectable marker genes for selection of transformed cells or tissues can include genes that confer antibiotic resistance or resistance to herbicides. Examples of suitable selectable marker genes include, but are not limited to, genes encoding resistance to chloramphenicol (Herrera Estrella et al. (1983) *EMBO J.* 2:987–992); methotrexate (Herrera Estrella et al. (1983) *Nature* 303:209–213; Meijer et al. (1991) *Plant Mol. Biol.* 16:807–820); hygromycin (Waldron et al. (1985) *Plant Mol. Biol.* 5:103–108; Zhijian et al. (1995) *Plant Science* 108:219–227); streptomycin (Jones et al. (1987) *Mol. Gen. Genet.* 210:86–91); spectinomycin (Bretagne-Sagnard et al. (1996) *Transgenic Res.* 5:131–137); bleomycin (Hille et al. (1990) *Plant Mol. Biol.* 7:171–176); sulfonamide (Guerineau et al. (1990) *Plant Mol. Biol.* 15:127–136); bromoxynil (Stalker et al. (1988) *Science* 242:419–423); glyphosate (Shaw et al. (1986) *Science* 233:478–481); phosphinothricin (DeBlock et al. (1987) *EMBO J.* 6:2513–2518).

Other genes that could serve utility in the recovery of transgenic events but might not be required in the final product would include, but are not limited to, examples such as GUS (b-glucoronidase; Jefferson (1987) *Plant Mol. Biol.*

Rep. 5:387), GFP (green florescence protein; Chalfie et al. (1994) Science 263:802), luciferase (Riggs et al. (1987) Nucleic Acid Res. 15 (19): 8115; Luchrsen et al. (1992) Methods Enzymol. 216: 397–414) and the maize genes encoding for anthocyanin production (Ludwig et al. (1990) Science 247:449).

The expression cassette comprising the particular promoter sequence of the present invention operably linked to a heterologous nucleotide sequence of interest can be used to transform any plant. In this manner, genetically modified plants, plant cells, plant tissue, pollen, and the like can be obtained. Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) Biotechniques 4:320–334), electroporation (Riggs et al. (1986) Proc. Natl. Acad. Sci. USA 83:5602–5606, Agrobacterium-mediated transformation (Townsend et al., U.S. Pat No. 5,563,055), direct gene transfer (Paszkowski et al. (1984) EMBO. J. 3:2717–2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in Plant Cell, Tissue, and Organ Culture. Fundamental Methods, ed. Gamborg and Phillips (Springer-Verlag, Berlin); and McCabe et al. (1988) Biotechnology 6:923–926). Also see Weissinger et al. (1988) Ann. Rev. Genet. 22:421–477; Sanford et al. (1987) Particulate Science and Technology 5:27–37 (onion); Christou et al. (1988) Plant Physiol. 87:671–674 (soybean); McCabe et al. (1988) Bio/Technology 6:923–926 (soybean); Finer and McMullen (1991) In Vitro Cell Dev. Biol. 27P: 175–182 (soybean); Singh et al. (1998) Theor. Appl. Genet. 96:319–324 (soybean); Datta et al. (1990) Biotechnology 8:736–740 (rice); Klein et al. (1988) Proc. Natl. Acad. Sci. USA 85:4305–4309 (maize); Klein et al. (1988) Biotechnology 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in Plant Cell, Tissue, and Organ Culture: Fundamental Methods, ed. Gamborg (Springer-Verlag, Berlin) (maize); Klein et al. (1988) Plant Physiol. 91:440–444 (maize); Fromm et al. (1990) Biotechnology 8:833–839 (maize); Hooykaas-Van Slogteren et al. (1984) Nature (London) 311:763–764; Bowen et al., U.S. Pat. No. 5,736,369 (cereals); Bytebier et al. (1987) Proc. Natl. Acad. Sci. USA 84:5345–5349 (Liliaceae); De Wet et al. (1985) in The Experimental Manipulation of Ovule Tissues, ed. Chapman et al. (Longman, New York), pp. 197–209 (pollen); Kaeppler et al. (1990) Plant Cell Reports 9:415–418 and Kaeppler et al. (1992) Theor. Appl. Genet. 84:560–566 (whisker-mediated transformation); D'Halluin et al. (1992) Plant Cell 4:1495–1505 (electroporation); Li et al. (1993) Plant Cell Reports 12:250–255 and Christou and Ford (1995) Annals of Botany 75:407–413 (rice); Osjoda et al. (1996) Nature Biotechnology 14:745–750 (maize via Agrobacterium tumefaciens); all of which are herein incorporated by reference.

The cells that have been transformed may be grown into plants in accordance with conventional ways. See, for example, McCormick et al. (1986) Plant Cell Reports 5:81–84. These plants may then be grown, and either pollinated with the same transformed strain or different strains, and the resulting hybrid having pollen-preferred expression of the desired phenotypic characteristic identified. Two or more generations may be grown to ensure that pollen-preferred expression of the desired phenotypic characteristic is stably maintained and inherited and then pollens harvested to ensure pollen-preferred expression of the desired phenotypic characteristic has been achieved.

The following examples are offered by way of illustration and not by way of limitation.

EXPERIMENTAL

Promoter region for the sunflower gene SF3 was isolated and cloned. The gene was selected as a source of pollen-preferred promoter based on the spatial expression of its gene product. The method for the isolation and expression is described below.

Example 1

Isolation of Promoter Sequences of Sunflower SF3 Promoter from Genomic Clone and Construction of Expression Vectors The SF3 gene was isolated by high stringency hybridization screening of a sunflower genomic library using the SF3 cDNA as a probe. The library DNA was from hypocotyls from the sunflower line HA401B. The vector used for the construction of the genomic library was the lambda phage derivative Charon40, See Dunn and Blattner (1987) Nucleic Acids Res. 15:2677–2698, herein incorporated by reference. A positive clone with a 14 kbp insert was restriction mapped, and two adjacent fragments containing the coding sequence for SF3 were identified by Southern hybridization and subcloned into pUC19. These fragments were denominated 3.11 and 3.61. Sequence analysis and comparison with the cDNA sequence showed that fragment 3.11 contains the 3' end of the gene while fragment 3.61 contains almost the entire translated sequence and approximately 800 bp of the upstream region including the promoter. The transcription start site was determined by primer extension on pollen polyA RNAs using a 5'-labeled oligonucleotide from the 5' region of the coding sequence ($^{32}$P-5'-CTGTGCATTTTTGGGTTGTTCCTGTGAATGA-3'; SEQ ID NO:4). When the primer extension products were run on a sequencing gel along with the products of the four DNA sequencing reactions performed using the same oligonucleotide, a single strong band was observed at the position defined as transcription start site or position 825 in the sequence shown in SEQ ID NO: 2.

A genomic subclone pHA3.61 from sunflower (Helianthus annuus), comprising most of the SF3 gene as a 1.9 Kb insert in pUC19 (Yanisch-Perron et al. (1985) Gene 33: 103–119), was subcloned into pBluescript SK$^+$ (Stratagene). The insert comprised 1 Kb of DNA from 824 base pairs upstream to 176 bp downstream of the start of transcription. This 1 kb insert is shown in SEQ ID NO: 2. The 39-mer PHN57, having the sequence CAATAACCA-CAAGAAAACCATGGAATCATTCACAGGAAC (SEQ ID NO: 5), was used in single-stranded site-directed mutagenesis according to the method of Su and El-Gewely ((1988) Gene 69: 81–89) to introduce a convenient restriction site at the start of translation in the SF3 fragment.

Figure 2:
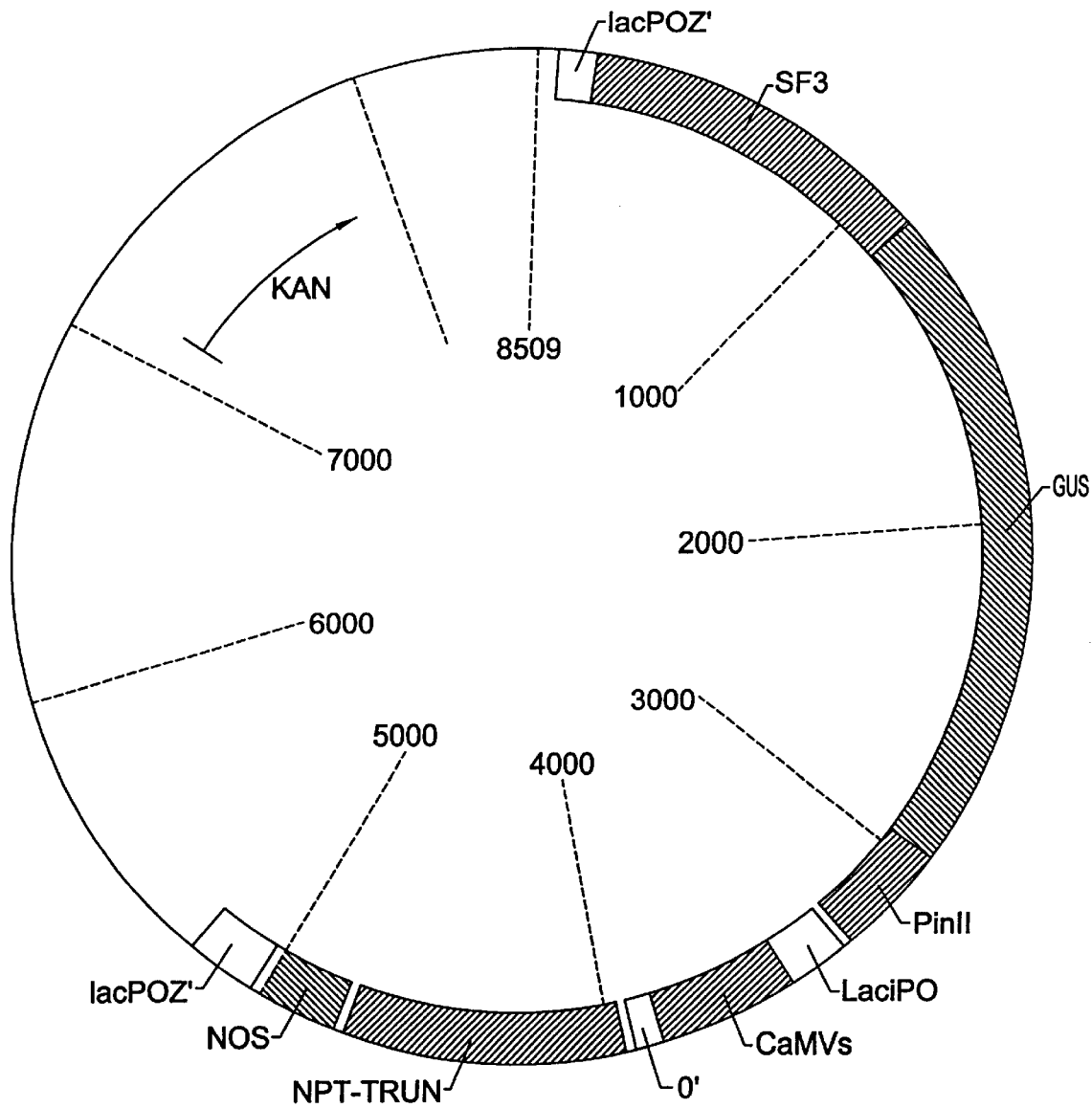
FIG. 2 schematically depicts a construct comprising plant transcription units PSF3:GUS:PINII-3', and PCaMV355:Q:NPTII:NOS-3' which is the kanamycin resistance plant transcription unit.
Figure 3:
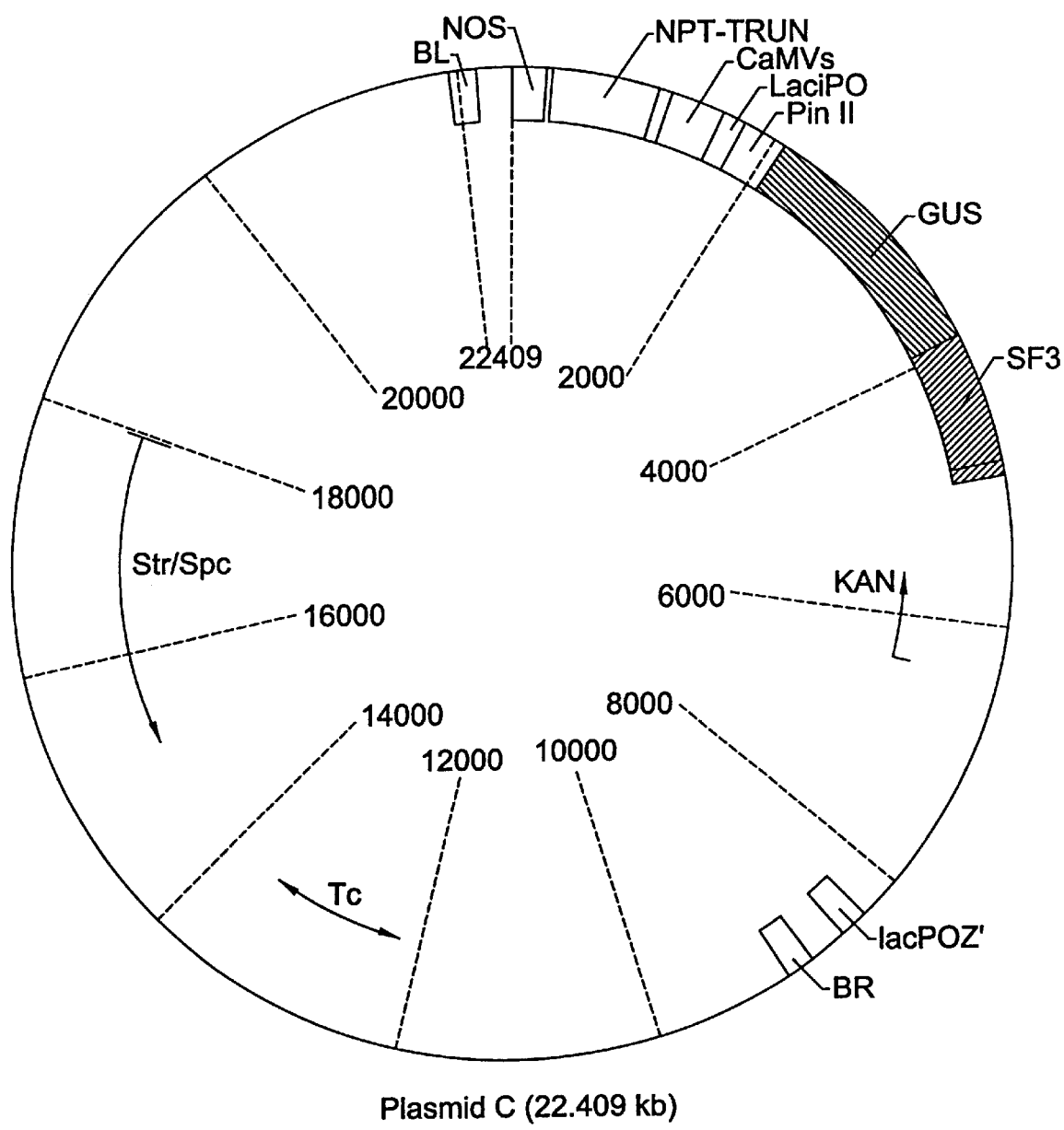
FIG. 3 schematically depicts a construct comprising the SF3 promoter and Gus reporter used in pollen-preferred expression of Gus.

The portion of the SF3 gene downstream of the start of translation was then removed by digestion and replaced with a 2.2 Kb fragment. This fragment contained the open reading frame of the UidA gene from E. coli encoding the β-Glucuronidase (GUS) protein, fused to the 3' nontranslated region of the proteinase inhibitor II gene (PinII) from potato (*Solanum tuberosum*). The resulting construct Plasmid A (FIG. 1), comprised 928 bp of the sunflower SF3 gene, including the promoter and nontranslated 5' leader, operably linked to the GUS-encoding UidA ORF and PinII 3' region. This plant transcription unit (PTU), designated by the notation pSF3:GUS:PinII-3', was cloned into a vector containing a chimeric PTU conferring kanamycin resistance in plants, as well as a separate bacterial kanamycin resistance gene, to yield Plasmid B (FIG. 2). The kanamycin resistance PTU is designated pCaMV35S:Ω': NPTII:Nos-3', in which pCaMV35S refers to the promoter for the 35S transcript from Cauliflower Mosaic Virus (Strassbourg strain), which is operably linked via the Tobacco Mosaic Virus nontranslated leader Ω' to NPTII, the open reading frame of the neomycin phosphotransferase type II gene from Tn5, isolated from Klebsiella; and Nos-3', the 3' nontranslated region of the nopaline synthase gene from *Agrobacterium tumefaciens* C58. Plasmid B was then inserted into a T-DNA vector by appropriate restriction digestion and ligation. The result was a T-DNA vector containing pSF3:GUS:PinII-3' and the selectable marker pCaMV35S:Ω': NPTII:Nos-3' within the T-DNA borders, with the GUS PTU closer to the right border and both PTUs oriented with the direction of transcription towards the left T-DNA border. This construct was designated Plasmid C (FIG. 3).

Example 2

Expression Using Pollen-Preferred Promoter Sequences

The intact meristem method is used for transformation of sunflower plants and expression of the GUS gene comprised by the construct Plasmid C (FIG. 3 and Example 1) as follows:

Explant Preparation:

Seeds are dehulled and surface-sterilized for 20 minutes in a 20% Chlorox™ bleach solution with the addition of two to three drops of Tween 20 per 100 ml of solution, and then rinsed three times with distilled water. Sterilized seeds are imbibed in the dark at 26° C. for 20 hours on filter paper moistened with water. Meristem explants are created by removing cotyledons and root radicle from imbibed seeds, and then culturing overnight at 26° C. in the dark on 374E medium (1×MS salts, Shepards vitamins, 40 mg/l adenine sulfate, 30 g/l sucrose, o.5 mg/l BAP, 0.25 mg/l IAA, 0.1 mg/l IAA, pH 5.6, 8g/l phytagar). Primary leaves are then removed and explants are transferred to 374M medium (374E except 12 g/l phytagar), arranged in a manner suitable for particle gun bombardment, and cultured overnight at 26° C. in the dark.

Transformation:

Approximately 18.8 mg of 1.8 $\mu$m tungsten particles are suspended in 150 $\mu$l absolute ethanol, and sonicated for 2–4 seconds. After sonication, 10 $\mu$l of the suspension is dropped on the center of the surface of a macrocarrier. Each plate of meristem explants is bombarded twice with 650 psi rupture discs in the top shelf at 26 mm of Hg helium gun vacuum, using a BioRad helium gun.

Plasmid C is introduced into Agrobacterium strain EHA 105 (see above) via freeze-thawing as described by Holsters et al. (1978) *Mol. Gen. Genet.* 163:181–187. Actively growing, transformed Agrobacteria were maintained in shaking liquid cultures using 60A medium with kanamycin (YEP, 50 mg/l kanamycin: 10 g/l yeast extract, 10 g/l bactopeptone, 5 g/l NaCl, pH 7.0, 50 mg/l kanamycin). On the day before the Agrobacterium strain is to be used, new liquid cultures are initiated in 60A with kanamycin from the active maintenance culture. They are cultured with shaking at 26° C. until they reach an optical density (OD vis=600 nm) of about 1.0. When the cultures have established this density, they are centrifuged (6000 rpm, 5 min), the supernatant is discarded, and the pellet of bacteria is resuspended in inoculation medium (12.5mM 2-(N-morpholino) ethanesulfonic acid, 1 g/l NH4C1, and 0.3 g/l MgSO4, at pH 5.7), to a final calculated concentration of Agrobacteria of 4.0 at OD 600. The particle bombarded explants are inoculated with Agrobcterium by first spreading the explants apart on the 374M medium, then placing a droplet of the above suspension directly onto the top of each meristem. The explants are co-cultivated on the medium for 4 days, after which the explants are transferred to 374 C medium (GBA with 1% sucrose and with no BAP, IAA, or GA3, and supplemented with 250 $\mu$g/ml cefotaxime). The explants are cultured on this medium for about 2 weeks under 16 hours of daylight, at 26° C.

Recovering Nodes and Plants:

Following the 4 days of co-cultivation time on 374M medium, the explants are transferred to 374D (374C medium with 50 mg/l kanamycin) selection medium containing kanamycin. After 2 weeks of selection, explants with associated shoots are transferred to 374C medium and selection resistant shoots are screened using NPTII ELISA. Positive shoots are removed for recovery by in vitro grafting and transformation verified by further NPTII ELISA analysis. Negative shoots are discarded. Explants with smaller shoots which could not be assayed following the 2 weeks on 374D are transferred to 374G (374E with 250 mg/l cefotaxime) for 3–4 days then back to 374C for 2 additional weeks. Assays are then done to identify positive shoots which are too small to sample in the first round and recovery initiated. Recovered positive shoots are grafted to Pioneer sunflower hybrid in vitro-grown sunflower seedling rootstock. The seeds are dehulled and surface-sterilized for 20 minutes in a 20% Chlorox™ bleach solution with two to three drops of Tween20 per 100 ml total volume, and rinsed three times with distilled water. The sterilized seeds are germinated for three days on filter paper moistened with water, then transferred into "48 Medium" (one-half strength MS salts, 0.5% sucrose, 0.3% gelrite, at pH 5.0) and grown at 26° C. in the dark for 3 days, then incubated at 16 hour day culture conditions. The upper portions of selected seedlings are removed, a vertical slice is made in each hypocotyl, and a transformed shoot is inserted into the vertical slice. The cut area is wrapped with parafilm, and after one week culture on the medium, the grafted plants are transferred to soil. In the first two weeks they are maintained under high humidity conditions to acclimatize to the greenhouse environment.

Transformed sectors of TO plants are identified by additional NPTII assays of the greenhouse established positive grafted shoots. After assay, non-transformed sectors are trimmed off to promote auxillary bud development and auxiliary buds from transgenic sectors are recovered so as to establish the best probability to encompass the sector of transformation in germ line cells so that the transformation event is recovered in the next generation. Seed from TO plants are collected, de-hulled, surface sterilized, and germinated on filter paper wetted with water. T1 seedlings are then sampled for NPTII ELISA by removing green cotyledon pieces followed by transfer to seedling growth medium 48P (0.1×MS salts, 0.5% sucrose, pH 5.6, 0.3% gelrite). NPTII positive, actively growing T1 seedlings are transferred at the two leaf stage to soil for growth in the greenhouse. Seed from the confirmed T1 transgenics is used to grow T2 plants.

T2 seeds are planted in a greenhouse. Positive plants are screened by NPTII assay. Various plant tissues are harvested at 80-day-old stage after planting. The harvested material is put in mini-tubes, frozen and stored at −80° C.

SF3 promoter activity is measured by using the reporter gene GUS as described below.

As an alternative to the intact meristem method, the split embryonic axis method was used as described in Malone-Schoneberg et al. (1994) *Plant Science* 103:193–207, in transforming sunflower plants with Plasmid C (Example 1 and FIG. 3) and generating T2 plants expressing the GUS reporter gene in a pollen preferred manner. T2 seeds were planted in a greenhouse and positive plants were screened by NPTII assay. Plant tissues were harvested at 80-day-old stage after planting. The harvested material was put in mini-tubes, frozen, and stored at −80° C.

SF3 Promoter Activity

SF3 promoter activity was measured by using the reporter gene GUS. GUS activity in various tissues was measured by fluorogenic assay. The fluorogenic assay determines the specific activity of P-glucuronidase (GUS) in various sunflower tissue extracts. The specific activity of the enzyme is expressed as moles of 4-methyl umbelliferone (MU) released/µg protein/hour. MU is produced when the enzyme (GUS) in plant cell extracts cleaves the glucuronide moiety from the 4-methyl umbelliferyl-β-D-glucuronide (MUG) substrate.

Harvested T2 tissue samples stored at −80° C. were homogenized in 400 µl lysis buffer (40 mM Phosphate, pH 7.0, 10 mM EDTA, 10 mM β-mercaptoehtanol), and then centrifuged in the Jouan GR422 centrifuge for 10 minutes at 4000 rpm. The total protein concentration of the supernatant was measured using the Bio-Rad Bradford Method (Bio-RAD) with BSA as the standard protein according to manufacture's protocol. Ten µl of diluted supernatant (about 4 µg of total protein) was used for the GUS activity assay. GUS activity was assayed according to Jefferson et al.(1987) *EMBO J.* 6; 3901–3907 using MUG as substrate.

Figure 4:
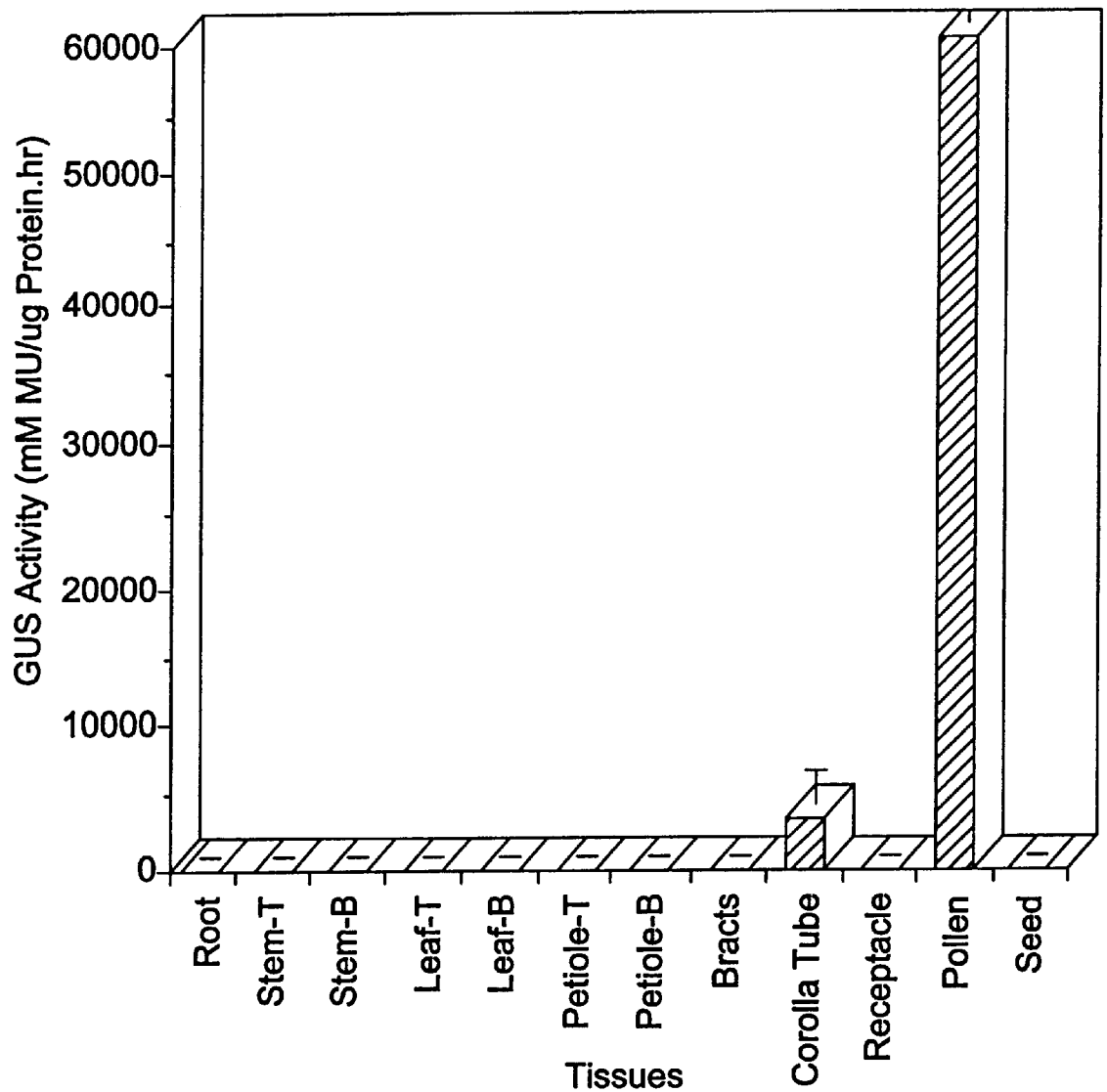
FIG. 4 depicts pollen-preferred expression of Gus in sunflower tissues.

The GUS activities in various tissues were summarized in FIG. 4. The data are the mean of 4 events with 6 plants from each event. The error bars are the SE. Tissue designations are as follows: Root, lateral root tissue; Stem-T, Phloem tissue from top part of stem; stem-B, phloem tissue from bottom part of stem; T denotes top part; B denotes bottom part; pollen, developing pollen; seed, 10 day after pollination.

As shown in FIG. 4, SF3 highly expresses GUS in pollen tissues. There is some GUS activity in corolla tube that is 6% of that activity in pollen. Very low activities were detected in other tissues. The moderate activity in corolla tube tissues may be caused by trace amount of pollen tissues that was not separated from the corolla tube. The SF3: GUS expression results are consistent with the Northern blot assay that indicated that SF3 gene was only highly expressed in pollen. See Baltz et al. (1992) *Plant J.* 2: 713–721.

These results indicate that SF3 is a strong pollen-specific promoter which can be used to highly express transgenes in sunflower pollen. SF3 promoter also can be used to express transgenes in pollen of other plants.

Example 3

Pollen Preferred Expression Of a Gene Involved In Resistance To Insects

A vector construct is made by the methods described in Example 1 for Plasmid C, except that a gene encoding Bacillus thuringiensis endotoxin (Btx) is substituted for the GUS gene as the heterologous DNA of interest. Sunflower plants expressing the Btx protein in a pollen-preferred manner are generated according to methods described in Example 2.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An isolated nucleic acid molecule having a nucleotide sequence that drives transcription in a plant cell, wherein said nucleotide sequence is set forth in SEQ ID NO: 1.

2. A DNA construct comprising the isolated nucleic acid molecule of claim 1 operably linked to a heterologous nucleotide sequence of interest.

3. A vector comprising the DNA construct of claim 2.

4. A host cell stably transformed with the vector of claim 3.

5. The host cell of claim 4, wherein said host cell is a plant cell.

6. A plant cell stably transformed with a DNA construct comprising a heterologous nucleotide sequence operably linked to a nucleic acid molecule that drives transcription in a plant cell wherein said nucleic acid molecule comprises the nucleotide sequence set forth in SEQ ID NO: 1.

7. The plant cell of claims 6, wherein said plant cell is from a dicot.

8. The plant cell of claim 7, wherein said dicot is sunflower.

9. The plant cell of claim 6, wherein said plant cell is from a monocot.

10. The plant cell of claim 9, wherein said monocot is maize.

11. A method for expressing a first nucleotide sequence in plant pollen, said method comprising:

transforming a plant cell with a DNA construct comprising said first nucleotide sequence operably linked to a second nucleotide sequence comprising the nucleotide sequence set forth in SEQ ID NO: 1; and regenerating a stably transformed plant from said transformed plant cell.

12. A plant stably transformed with a DNA construct comprising a heterologous nucleotide sequence operably linked to a nucleic acid molecule that drives transcription in a plant cell, and wherein said nucleic nucleotide sequence set forth in SEQ ID NO: 1.

* * * * *

UNITED STATES PATENT AND TRADEMARK OFFICE
CERTIFICATE OF CORRECTION

PATENT NO.   : 6,452,069 B1
DATED        : September 17, 2002
INVENTOR(S)  : Baltz et al.

It is certified that error appears in the above-identified patent and that said Letters Patent is hereby corrected as shown below:

Title page,
Item [73], Assignee, insert: -- Centre National de la Recherche Scientifique, Paris (FR) --.

Column 23,
Line 45, "claims 6" should read -- claim 6 --.

Column 24,
Line 45, after "nucleic" insert -- acid molecule comprises the --.

Signed and Sealed this

Eighth Day of April, 2003

JAMES E. ROGAN
*Director of the United States Patent and Trademark Office*

SEQUENCE LISTING

```
<160> NUMBER OF SEQ ID NOS: 5

<210> SEQ ID NO 1
<211> LENGTH: 824
<212> TYPE: DNA
<213> ORGANISM: Helianthus annus

<400> SEQUENCE: 1
gatccgatga tacccgaacg tttttgctta tatatcatct aatttaaatt taaataacta     60
tgattagagg aacattcata ttttaaaatg gataaacacg aatgggacat attgaaaata    120
taaaatatat ggaccaatct aaatgagtca tgttatcgga atattccttc ccaatgttat    180
atgtgttaga tgcatacttt ttagtcatca catcagtcca ttagctatgt gtagcatagt    240
catagcagtt tttaaagacc gtataccttt acatgagcat atgcacgttg gctgccctat    300
actggcatat cctgtaccat acaacactct atgcgagtgt acacgatata ccctcaaatc    360
aatagggtgt tgattggtaa cgcagatgag atgacgtgtg tataatctct cctggtttaa    420
```

```
cttggtgtgg taaagtacga aactagatcc ctaattgtat ggcaattgac tctcttaayc    480
atgttagtca tgtaatacta ttagatttta gaattttctt ggtatcctta ttccattttg    540
ttttaggaca aagagtcata gaaaggtaat aattgtacaa ttcagttatt taatttata     600 ttctcatttt cagtaaagat tttagattat ttgaaatctt tttttatcgg taatatagtt    660
tctaaaaata taaaaggaaa ggaaaggaaa acaacaggaa atgcatgaag atcggatcaa    720
agaatgggtg ttgataactc ttttttttt  ccttaatttg ctgcaatcca cacaccaaca    780 attttttcatc tcttttttaaa ggacatgaaa atcatgattc aagt                   824
```

```
<210> SEQ ID NO 2
<211> LENGTH: 1000
<212> TYPE: DNA
<213> ORGANISM: Helianthus annus
<220> FEATURE:
<221> NAME/KEY: promoter
<222> LOCATION: (1)...(824)
<221> NAME/KEY: misc_feature
<222> LOCATION: (825)...(825)
<223> OTHER INFORMATION: Transcription Start Site begins at base No. 825
<220> FEATURE:
<221> NAME/KEY: CDS
<222> LOCATION: (929)...(1000)

<400> SEQUENCE: 2
```

```
gatccgatga tacccgaacg ttttttgctta tatatcatct aatttaaatt taaataacta    60
tgattagagg aacattcata ttttaaaatg gataaacacg aatgggacat attgaaaata    120
taaaatatat ggaccaatct aaatgagtca tgttatcgga atattccttc ccaatgttat    180
atgtgttaga tgcatacttt ttagtcatca catcagtcca ttagctatgt gtagcatagt    240
catagcagtt ttttaaagacc gtataccttt acatgagcat atgcacgttg gctgccctat    300
actggcatat cctgtaccat acaacactct atgcgagtgt acacgatata ccctcaaatc    360 aataggggtgt tgattggtaa cgcagatgag atgacgtgtg tataatctct cctggtttaa    420
cttggtgtgg taaagtacga aactagatcc ctaattgtat ggcaattgac tctcttaayc    480
atgttagtca tgtaatacta ttagatttta gaattttctt ggtatcctta ttccattttg    540
ttttaggaca aagagtcata gaaaggtaat aattgtacaa ttcagttatt taatttata     600 ttctcatttt cagtaaagat tttagattat ttgaaatctt tttttatcgg taatatagtt    660
tctaaaaata taaaaggaaa ggaaaggaaa acaacaggaa atgcatgaag atcggatcaa    720
agaatgggtg ttgataactc ttttttttt  ccttaatttg ctgcaatcca cacaccaaca    780 attttttcatc tcttttttaaa ggacatgaaa atcatgattc aagtacaaaa caataaagga   840
gtttcttgag agttcagagt tctttttcttt gcgttattta tccaaataac aagagaaaaa    900
gaactctttc aataaccaca agaaaaaaa atg aaa tca ttc aca gga aca acc      952
                                  Met Lys Ser Phe Thr Gly Thr Thr
                                   1               5 caa aaa tgc aca gtt tgc gag aaa acc gtg tat ttg gtt gat aaa tta     1000
Gln Lys Cys Thr Val Cys Glu Lys Thr Val Tyr Leu Val Asp Lys Leu
    10              15                  20
```

```
<210> SEQ ID NO 3
<211> LENGTH: 24
<212> TYPE: PRT
<213> ORGANISM: Helianthus annus
```

```
<400> SEQUENCE: 3

Met Lys Ser Phe Thr Gly Thr Thr Gln Lys Cys Thr Val Cys Glu Lys
  1               5                  10                  15

Thr Val Tyr Leu Val Asp Lys Leu
             20

<210> SEQ ID NO 4
<211> LENGTH: 31
<212> TYPE: DNA
<213> ORGANISM: Helianthus annus

<400> SEQUENCE: 4
ctgtgcattt ttgggttgtt cctgtgaatg a                              31

<210> SEQ ID NO 5
<211> LENGTH: 39
<212> TYPE: DNA
<213> ORGANISM: Helianthus annus

<400> SEQUENCE: 5
caataaccac aagaaaacca tggaatcatt cacaggaac                      39
```